US008942829B2

(12) United States Patent
Rothstein et al.

(10) Patent No.: US 8,942,829 B2
(45) Date of Patent: Jan. 27, 2015

(54) TRANS-SEPTAL LEAD ANCHORING

(75) Inventors: Paul T. Rothstein, Elk River, MN (US);
Martin J. Clements, Rogers, MN (US);
Michael W. Kimmel, Edina, MN (US);
Steven L. Waldhauser, White Bear Township, MN (US)

(73) Assignee: Medtronic, Inc., Minneapolis, MN (US)

( * ) Notice: Subject to any disclaimer, the term of this patent is extended or adjusted under 35 U.S.C. 154(b) by 342 days.

(21) Appl. No.: 13/009,972

(22) Filed: Jan. 20, 2011

(65) Prior Publication Data

US 2012/0191169 A1    Jul. 26, 2012

(51) Int. Cl.
*A61N 1/00* (2006.01)
*A61N 1/05* (2006.01)

(52) U.S. Cl.
CPC ................................... *A61N 1/0573* (2013.01)
USPC .......................................................... 607/127

(58) Field of Classification Search
CPC ....... A61N 1/053; A61N 1/057; A61N 1/056; A61N 1/05; A61N 1/0573; A61B 2019/4836; A61B 17/0057; A61B 17/0469
USPC .......................... 607/119, 126–128, 130–131
See application file for complete search history.

(56) References Cited

U.S. PATENT DOCUMENTS

| | | | |
|---|---|---|---|
| 3,750,650 A * | 8/1973 | Ruttgers | ........................ 600/376 |
| 4,884,567 A | 12/1989 | Elliott et al. | |
| 4,898,156 A | 2/1990 | Gatturna et al. | |
| 5,002,563 A | 3/1991 | Pyka et al. | |
| 5,108,420 A | 4/1992 | Marks | |
| 5,127,421 A | 7/1992 | Bush et al. | |
| 5,203,787 A | 4/1993 | Noblitt et al. | |
| 5,336,252 A | 8/1994 | Cohen | |
| 5,397,343 A | 3/1995 | Smits | |
| 5,454,834 A | 10/1995 | Boebel et al. | |
| 5,478,354 A | 12/1995 | Tovey et al. | |
| 5,522,875 A * | 6/1996 | Gates et al. | .................... 607/127 |
| 6,002,969 A | 12/1999 | Machek et al. | |
| 6,080,182 A | 6/2000 | Shaw et al. | |
| 6,200,303 B1 | 3/2001 | Verrier et al. | |
| 6,391,038 B2 | 5/2002 | Vargas et al. | |
| 6,443,957 B1 | 9/2002 | Addis | |
| 6,491,707 B2 | 12/2002 | Makower et al. | |
| 6,772,014 B2 * | 8/2004 | Coe et al. | ....................... 607/119 |
| 6,776,784 B2 | 8/2004 | Ginn | |
| 6,909,920 B2 | 6/2005 | Lokhoff et al. | |

(Continued)

FOREIGN PATENT DOCUMENTS

WO    96/03925 A1    2/1996
WO    98/29040 A1    7/1998

(Continued)

OTHER PUBLICATIONS

Rothstein, et al., "Surgical Fastening Clips, Systems and Methods for Proximating Tissue", U.S. Appl. No. 12/039,629, filed Feb. 28, 2008, 33 pages.

*Primary Examiner* — Catherine Voorhees
(74) *Attorney, Agent, or Firm* — Evans M. Mburu

(57) ABSTRACT

Methods, devices and assemblies for anchoring implanted medical electrical leads employed in the stimulating and/or sensing of signals in tissue are disclosed. The devices include a lead anchoring clip having a central hub portion, an anchoring portion for coupling to tissue and a lead engagement mechanism that couples the clip to a medical electrical lead.

5 Claims, 10 Drawing Sheets

(56) References Cited

U.S. PATENT DOCUMENTS

| | | |
|---|---|---|
| 6,988,007 B1 | 1/2006 | Morgan et al. |
| 7,112,207 B2 | 9/2006 | Allen et al. |
| 7,149,587 B2 | 12/2006 | Wardle et al. |
| 7,155,294 B2 * | 12/2006 | Alinder .................. 607/127 |
| 7,220,268 B2 | 5/2007 | Blatter |
| RE39,897 E | 10/2007 | Mower |
| 7,321,798 B2 | 1/2008 | Muhlenberg et al. |
| 7,326,219 B2 | 2/2008 | Mowry et al. |
| 7,369,901 B1 * | 5/2008 | Morgan et al. ............ 607/127 |
| 2002/0013605 A1 | 1/2002 | Bolduc et al. |
| 2004/0153101 A1 | 8/2004 | Bolduc et al. |
| 2004/0225300 A1 | 11/2004 | Goldfarb et al. |
| 2006/0064116 A1 | 3/2006 | Allen et al. |
| 2006/0235445 A1 | 10/2006 | Birk et al. |
| 2006/0287661 A1 | 12/2006 | Bolduc et al. |
| 2007/0073337 A1 | 3/2007 | Abbott et al. |
| 2007/0270905 A1 | 11/2007 | Osborne |
| 2009/0222026 A1 | 9/2009 | Rothstein et al. |
| 2010/0042189 A1 * | 2/2010 | Jarl et al. .................. 607/116 |

FOREIGN PATENT DOCUMENTS

| | | |
|---|---|---|
| WO | 00/07506 A2 | 2/2000 |
| WO | 03084433 A2 | 10/2003 |
| WO | 2005107850 A1 | 11/2005 |
| WO | 2007038646 A1 | 4/2007 |

* cited by examiner

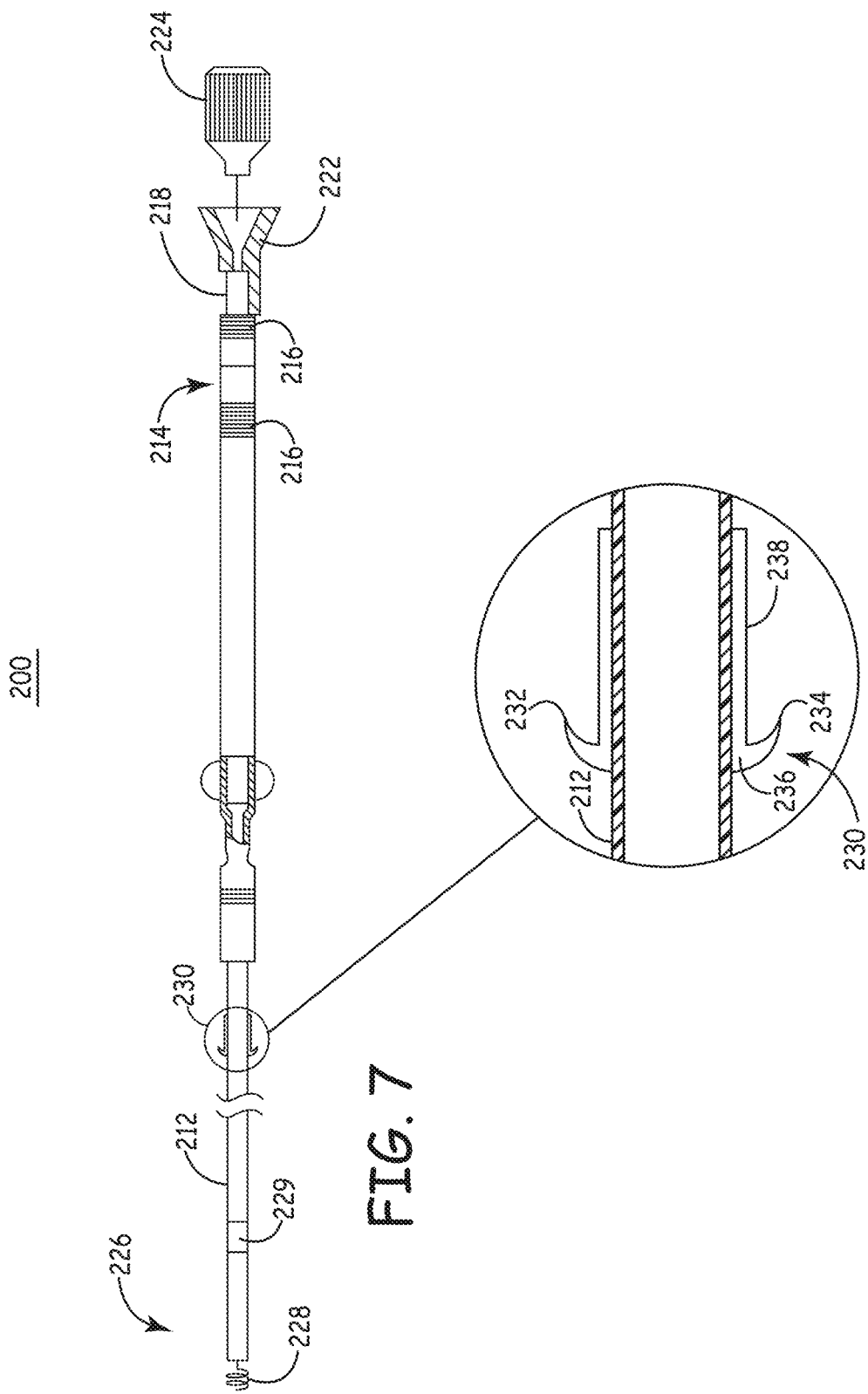

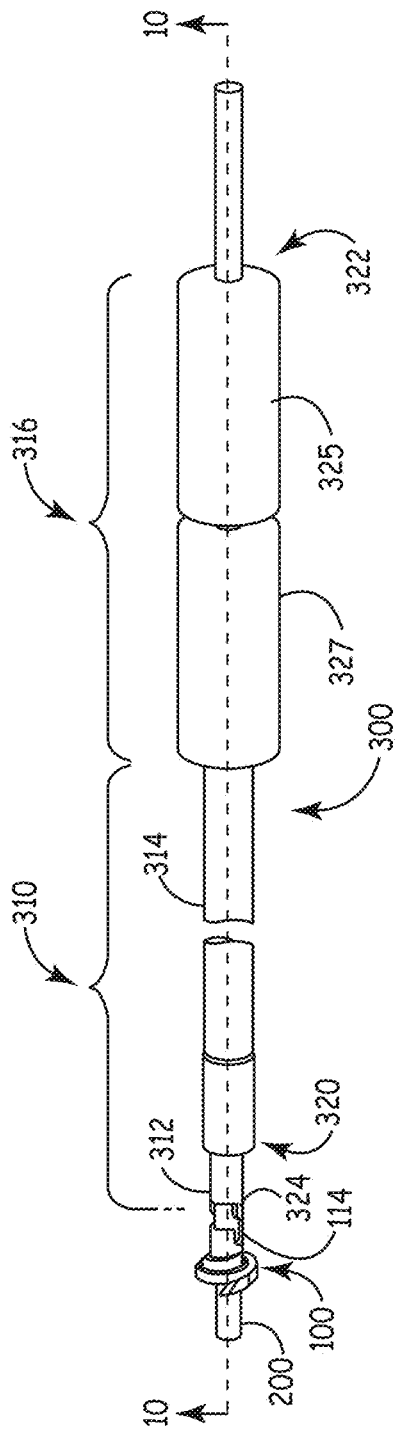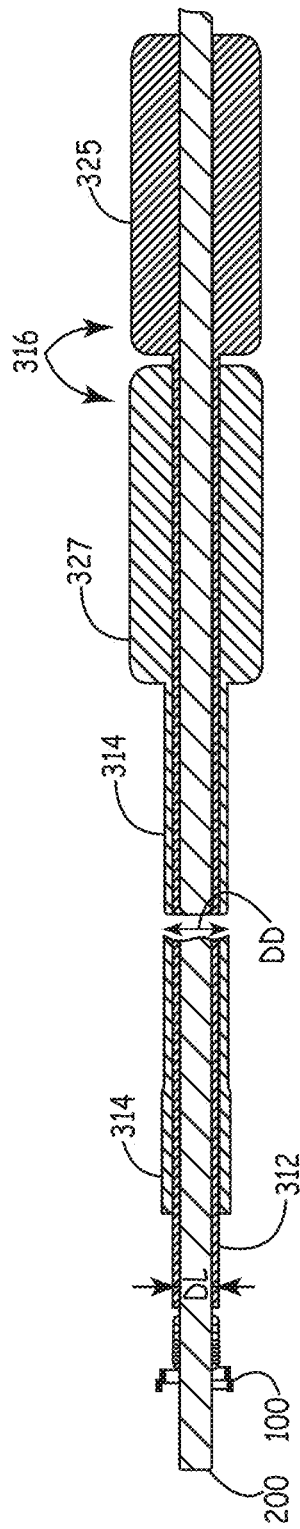

TRANS-SEPTAL LEAD ANCHORING

FIELD

The present disclosure relates generally to devices and methods for stimulating and/or sensing electrical signals in muscle tissue. More particularly, it relates to assemblies for anchoring implanted medical electrical leads employed in the stimulating and/or sensing of signals in the tissue.

BACKGROUND

In the medical field, various types of implantable medical electrical leads are known and used. For example, implantable medical devices (IMD) such as cardiac pacemakers, cardioverters, or defibrillators commonly have one or more implantable medical leads connecting the device to cardiac tissue. The leads coupling the devices to the cardiac muscle are commonly used for delivering an electrical pulse to the cardiac muscle, for sensing signals indicative of a physical parameter that may be produced in the cardiac muscle, or for both delivering and sensing.

The leads are susceptible to categorization according to the type of connection they form with the heart. An endocardial lead includes at least one electrode at or near its distal tip adapted to contact the endocardium (i.e., the tissue lining the inside of the heart). An epicardial lead includes at least one electrode at or near its distal tip adapted to contact the epicardium (i.e., the tissue lining the outside of the heart). Finally, a myocardial lead includes at least one electrode at or near its distal tip inserted into the heart muscle or myocardium (i.e., the muscle sandwiched between the endocardium and epicardium).

The lead typically consists of a flexible conductor surrounded by an insulating tube or sheath that extends from the electrode at the distal end to a connector pin at the proximal end. Some leads have multiple spaced apart distal electrodes at differing polarities and are known as bipolar type leads. The spacing between the electrodes can affect lead performance and the quality of the electrical signal transmitted or sensed through the heart tissue.

With the advancement in treatment of certain heart conditions such as congestive heart failure ("CHF"), there is often a need to perform multi-chamber stimulation. For example, cardiac resynchronization therapy ("CRT") (also commonly referred to as biventricular pacing) is one treatment for heart failure, which requires stimulation of right and left chambers to increase cardiac output. A common approach for accessing the left side of the heart is a transseptal access from the right atrium through the intra-atrial septum to the left atrium. U.S. Pat. No. 7,678,081, and U.S. Patent Application Publication 2007/0083168, both of which are incorporated herein by reference in their entirety, provide examples of catheter systems employing a right to left atrial transseptal approach. Once so inserted in a left side chamber, the distal end of the lead is positioned and often secured to tissue.

Typically, the distal end of a lead is electrically coupled with the endocardium by either an active anchoring mechanism or a passive anchoring mechanism. Passive anchoring mechanisms, such as a tine assembly, lodge or passively fix the lead to the heart. Active anchoring mechanisms use a structure, such as a helix or hook, to engage into or actively fix themselves to the heart.

While a large number of anchoring systems and methods are presently available, there remains a need for an improved medical electrical lead and attachment system suitable for minimizing shunting between chambers and minimizing lead motion for leads where access to target tissue may require puncturing through tissue, such as left-sided cardiac lead placement through a septal wall.

SUMMARY

Various conventional techniques are employed to secure the distal end of the lead within the heart. However, the inventors of this disclosure have discovered that certain drawbacks exist with respect to existing anchoring means that are specifically geared toward anchoring of the lead's distal tip. Therefore, in implants where leads are tunneled through the atrial and ventricular septal walls, the inventors have proposed an anchoring clip that creates a seal and fixates the lead at the point of access in a tissue wall separating heart chambers, for example. Accordingly, because the heart is a constantly moving organ, anchoring the lead at the septal wall minimizes motion of the fixated portion of the lead.

In accordance with principles of the present disclosure, a lead anchoring clip is disclosed. In an embodiment, the anchoring clip comprises a central hub portion formed integrally with/or coupled to a lead engagement mechanism and an anchoring portion. The engagement mechanism may define a tubular-like shape for engaging a lead. The engagement mechanism further includes a torque inducing detent that facilitates rotation of the lead anchoring clip. The anchoring portion may include a planar spiral wound portion defining a perimeter, a first leg projecting from the perimeter and a second leg also projecting from the perimeter. The first leg projects outwardly relative to the perimeter of the spiral portion from a point of departure to a tip. This projection establishes a spacing between the first leg and the perimeter. The second leg similarly projects outwardly relative to the perimeter from a point of departure to a tip, with a spacing being established between the second leg and the perimeter. Extension of each of the legs relative to the perimeter defines a wind direction that is either clockwise or counterclockwise, with the legs having identical wind directions. For example, the wind direction of both the first and second legs may be clockwise or counterclockwise.

In other embodiments, the spiral wound portion and the legs may combine to form the anchoring portion as having a hurricane-like shape. In yet other configurations, the lead anchoring clip may be formed from a tube having a double helix segment wherein the double helix is partially wound onto itself in a spiral-like fashion, with the spiral wound portion and the legs being co-planar in the undeflected state.

Other aspects in accordance with principles of the present disclosure relate to methods of securing a lead in cardiac tissue. Exemplary embodiments include securing the lead onto tissue via a lead anchoring clip by rotating the lead anchoring clip in a direction that causes tissue to gather in a spacing between each of the legs and a corresponding region of the perimeter. In the pre-deployment (undeflected) state, the first and second legs are relaxed outwardly from the perimeter whereas in the deployed state, the legs are wound closer to the perimeter.

Yet other aspects in accordance with principles of the present disclosure relate to a system for securing an implantable medical lead. The system includes a lead anchoring clip coupled to an implantable medical lead and a placement device for facilitating delivery and anchoring of the lead anchoring clip to a target site. In an example, the coupling between the lead and the lead anchoring clip may be achieved through constriction of a portion of the clip during or upon deployment. Alternatively, the lead anchoring clip may include a lead engagement mechanism for coupling with the lead such as by a frictional-fit engagement. The lead anchoring clip further includes an anchoring portion, a first leg, and a second leg. The anchoring portion may include a planar spiral wound portion defining a perimeter, with the first and second legs projecting outwardly relative to this perimeter in establishing a spacing between each of the legs and the perimeter. In this regard, extension of each of the legs relative to the perimeter defines a clockwise or counterclockwise wind direction, with the wind directions of the legs being identical.

In some embodiments, the placement device includes a sheath assembly and a handle assembly. The sheath assembly includes a drive tube sized to slidably receive at least a portion of the lead and engage a portion of the lead anchoring clip, with the drive tube being disposed within a sheath cover. The engagement between the lead anchoring clip and the drive tube may be through a detent and notch configuration. In some embodiments, the sheath cover and drive tube are akin to a catheter such that the anchoring clip can be deployed in a minimally invasive manner.

Other embodiments of the present disclosure pertain to a method of use of the system for securing an implantable medical lead. In use, the system is configured to provide a pre-deployment state in which the lead anchoring clip is releasably assembled to the distal region of the sheath. In the pre-deployment state, the anchoring clip is wound from the undeflected state to a collapsed state. Upon release of the anchoring clip from the sheath, the anchoring clip naturally transitions from the collapsed state toward the undeflected state in readiness for anchoring.

In an exemplary embodiment of the disclosure, the method includes providing a lead coupled to an anchoring clip that has an undeflected state, the anchoring clip including a lead engagement mechanism and an anchoring portion.

The anchoring clip may be coupled to the lead via an interference fit between the lead engagement mechanism and the outer perimeter of the lead.

The anchoring portion has a perimeter defining a planar spiral wound portion, along with first and second legs projecting outwardly relative to the perimeter. The legs extend in identical wind directions relative to the perimeter. The lead and anchoring clip sub-assembly is assembled to a placement device. In this regard, the anchoring clip is selectively retained in a distal region of the placement device. In the assembly, the sheath maintains the clip in a collapsed state. The anchoring clip is advanced, in the collapsed state, to a location adjacent the fixation site. The anchoring clip is transitioned from the collapsed state toward the undeflected state, for example by releasing the clip from the sheath. The anchoring clip is rotated via the retainer such that the tips pierce through the tissue adjacent to the fixation site. The anchoring clip is further rotated such that the tissue is gathered between each of the legs and a corresponding region of the center portion to at least anchor the clip to the tissue. In some embodiments, the method is performed in sealing an atrial septal wall, with a distal portion of the lead being advanced through the atrial septal wall from the right atrium into the left atrium.

BRIEF DESCRIPTION OF THE DRAWINGS

The following drawings are illustrative of particular embodiments of the present disclosure and therefore do not limit the scope of the disclosure. The drawings (not to scale) are intended for use in conjunction with the explanations in the following detailed description, wherein like reference numerals denote like elements throughout. Moreover, the specific location of the various features is merely exemplary unless noted otherwise.

FIG. 7 is a plan view of one embodiment of an improved lead employing a lead anchoring clip in accordance with principles of the present disclosure.

FIG. 8 is a cutaway side view of the lead anchoring clip and lead assembly of FIG. 7.

FIGS. 9 and 10 depict cross sectional views of an exemplary placement device for a lead and lead anchoring clip assembly.

DETAILED DESCRIPTION

The following description is exemplary in nature and is not intended to limit the scope, applicability, or configuration of the present disclosure in any way. Rather, the description provides practical illustrations for implementing exemplary embodiments of the present disclosure.

Figure 1:
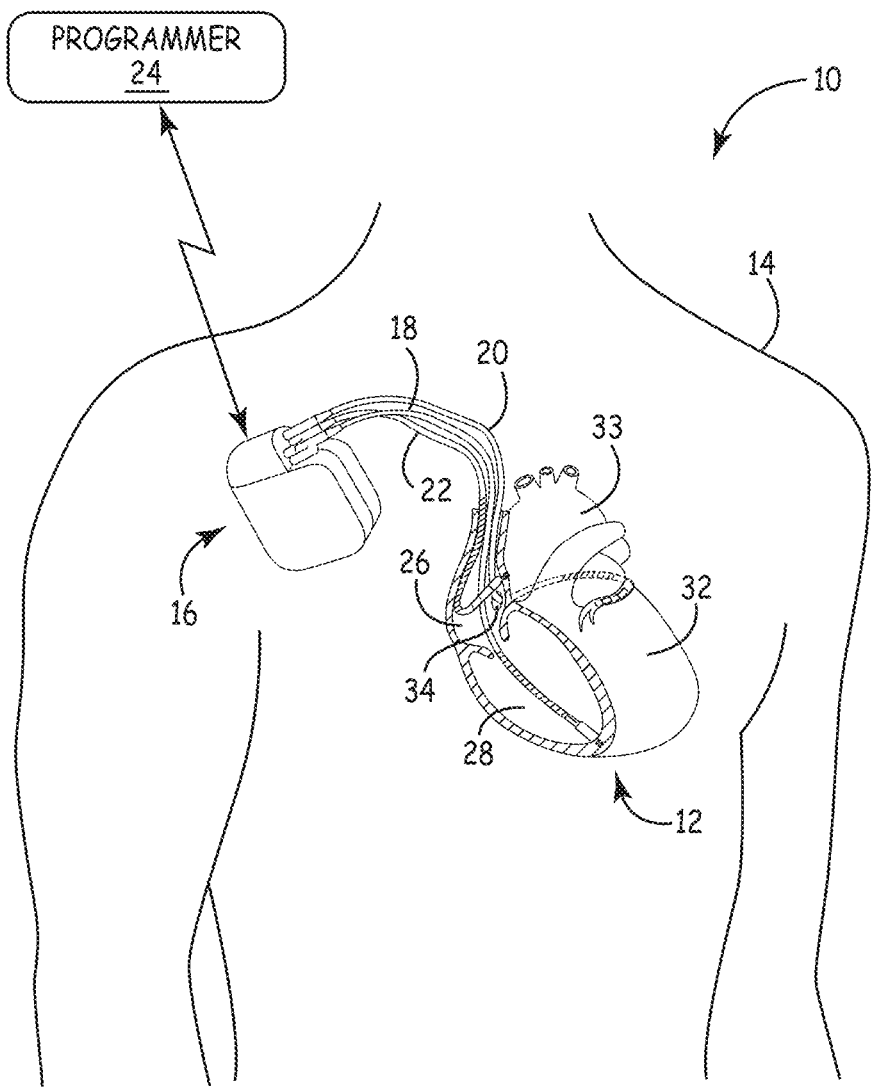
FIG. 1 is a conceptual diagram illustrating an example therapy system 10 that may be used to provide therapy to a heart of a patient.

FIG. 1 is a conceptual diagram illustrating an example therapy system 10 that may be used to provide therapy to heart 12 of patient 14. Patient 14 ordinarily, but not necessarily, will be a human. Therapy system 10 includes IMD 16, which is coupled to leads 18, 20, and 22, and programmer 24. IMD 16 may be, for example, an implantable pacemaker, cardioverter, and/or defibrillator that provides electrical signals to heart 12 via electrodes coupled to one or more of leads 18, 20, and 22. Each of leads 18, 20 and 22 may carry one or a set of electrodes. The electrode may extend about the circumference of each of leads 18, 20, and 22 and is positioned at a respective axial position along the length of each of the lead 18, 20, and 22.

Leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) lead 20 may extend through one or more veins, the vena cava, the right atrium 26, through the atrial septum 34 into the left atrium 33, and into the left ventricle 32 of heart 12. Right atrial (RA) lead 22 extends through one or more veins and the vena cava, and into the right atrium 26 of heart 12.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may also provide defibrillation therapy and/or cardioversion therapy via electrodes located on at least one of the leads 18, 20, 22. IMD 16 may detect arrhythmia of heart 12, such as fibrillation of ventricles 28 and 32, and deliver defibrillation therapy to heart 12 in the form of electrical pulses. In some examples, IMD 16 may be programmed to deliver a progression of therapies, e.g., pulses with increasing energy levels, until a fibrillation of heart 12 is stopped. IMD 16 detects fibrillation employing one or more fibrillation detection techniques known in the art.

In some examples, programmer 24 may be a handheld computing device or a computer workstation. Programmer 24 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some embodiments, a display of programmer 24 may include a touch screen display, and a user may interact with programmer 24 via the display.

A user, such as a physician, technician, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD.

For example, the user may use programmer 24 to retrieve information from IMD 16 regarding the rhythm of heart 12, trends therein over time, or tachyarrhythmia episodes. As another example, the user may use programmer 24 to retrieve information from IMD 16 regarding other sensed physiological parameters of patient 14, such as intracardiac or intravascular pressure, activity, posture, respiration, or thoracic impedance. As another example, the user may use programmer 24 to retrieve information from IMD 16 regarding the performance or integrity of IMD 16 or other components of system 10, such as leads 18, 20, and 22, or a power source of IMD 16.

The user may use programmer 24 to program a therapy progression, select electrodes used to deliver defibrillation shocks, select waveforms for the defibrillation shock, or select or configure a fibrillation detection algorithm for IMD 16. The user may also use programmer 24 to program aspects of other therapies provided by IMD 16, such as cardioversion or pacing therapies. In some examples, the user may activate certain features of IMD 16 by entering a single command via programmer 24, such as depression of a single key or combination of keys of a keypad or a single point-and-select action with a pointing device.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 2:
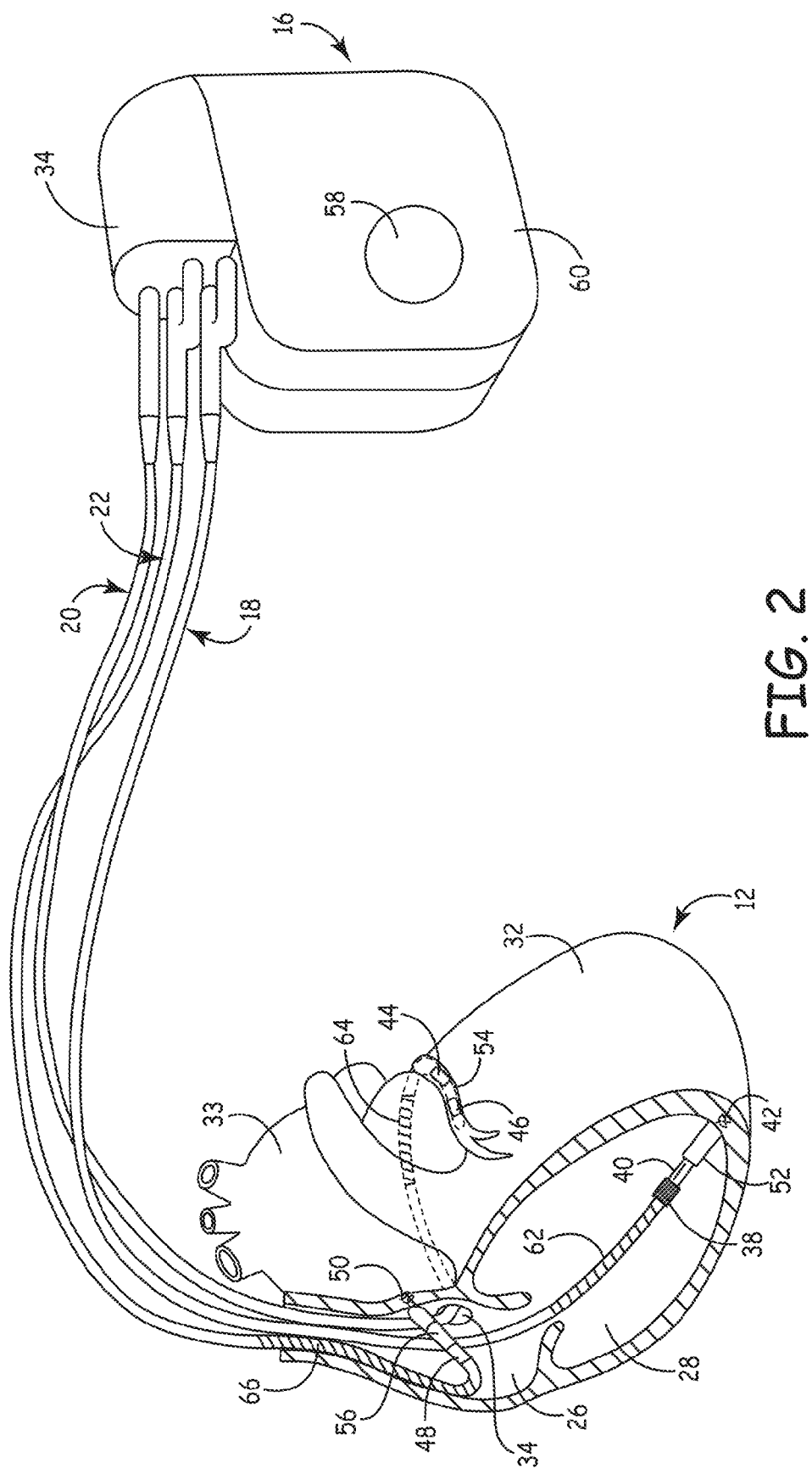
FIG. 2 is a conceptual diagram illustrating an implantable medical device and leads of therapy system 10 in greater detail.

FIG. 2 is a conceptual diagram illustrating IMD 16 and leads 18, 20, 22 of therapy system 10 in greater detail. Leads 18, 20, 22 may be electrically coupled to a stimulation generator, a sensing module, or other modules of IMD 16 via connector block 34. In some examples, proximal ends of leads 18, 20, 22 may include electrical contacts that electrically couple to respective electrical contacts within connector block 34. In addition, in some examples, leads 18, 20, 22 may be mechanically coupled to connector block 34 with the aid of set screws, connection pins or another suitable mechanical coupling mechanism.

Each of the leads 18, 20, 22 includes an elongated insulative lead body, which may carry a number of concentric coiled conductors separated from one another by tubular insulative sheaths. In the illustrated example, a pressure sensor 38 and bipolar electrodes 40 and 42 are located proximate to a distal end of lead 18. In addition, bipolar electrodes 44 and 46 are located proximate to a distal end of lead 20 and bipolar electrodes 48 and 50 are located proximate to a distal end of lead 22. In FIG. 2, pressure sensor 38 is disposed in right ventricle 28. Pressure sensor 30 may respond to an absolute pressure inside right ventricle 28, and may be, for example, a capacitive or piezoelectric absolute pressure sensor. In other examples, pressure sensor 30 may be positioned within other regions of heart 12 and may monitor pressure within one or more of the other regions of heart 12, or may be positioned elsewhere within or proximate to the cardiovascular system of patient 14 to monitor cardiovascular pressure associated with mechanical contraction of the heart.

Among the electrodes, some of the electrodes may be provided in the form of coiled electrodes that form a helix, while other electrodes may be provided in different forms. Further, some of the electrodes may be provided in the form of tubular electrode sub-assemblies that can be pre-fabricated and positioned over the body of leads 18, 20, 22, where they are attached and where electrical connections with conductive elements within the leads 18, 20, 22 can be made.

For example, electrodes 40, 44 and 48 may take the form of ring electrodes, and electrodes 42, 46 and 50 may take the form of extendable helix tip electrodes mounted retractably within insulative electrode heads 52, 54 and 56, respectively. Each of the electrodes 40, 42, 44, 46, 48 and 50 may be electrically coupled to a respective one of the coiled conductors within the lead body of its associated lead 18, 20, 22, and thereby coupled to respective ones of the electrical contacts on the proximal end of leads 18, 20 and 22.

Electrodes 40, 42, 44, 46, 48 and 50 may sense electrical signals attendant to the depolarization and repolarization of heart 12. The electrical signals are conducted to IMD 16 via the respective leads 18, 20, 22. In some examples, IMD 16 also delivers pacing pulses via electrodes 40, 42, 44, 46, 48 and 50 to cause depolarization of cardiac tissue of heart 12. In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. Any of the electrodes 40, 42, 44, 46, 48 and 50 may be used for unipolar sensing or pacing in combination with housing electrode 58. As is well known in the art, housing 60 may enclose a stimulation generator that generates cardiac pacing pulses and defibrillation or cardioversion shocks, as well as a sensing module for monitoring the patient's heart rhythm.

Leads 18, 20, 22 also include elongated electrodes 62, 64, 66, respectively, which may take the form of a coil. IMD 16 may deliver defibrillation shocks to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in implantable defibrillation electrodes.

Pressure sensor 38 may be coupled to one or more coiled conductors within lead 18. In FIG. 2, pressure sensor 38 is located more distally on lead 18 than elongated electrode 62. In other examples, pressure sensor 38 may be positioned more proximally than elongated electrode 62, rather than distal to electrode 62. Further, pressure sensor 38 may be coupled to another one of the leads 20, 22 in other examples, or to a lead other than leads 18, 20, 22 carrying stimulation and sense electrodes.

The configuration of therapy system 10 illustrated in FIGS. 1 and 2 is merely one example. In other examples, a therapy system may include epicardial leads and/or patch electrodes instead of or in addition to the leads 18, 20, 22 illustrated in FIG. 1. Further, IMD 16 need not be implanted within patient 14. In examples in which IMD 16 is not implanted in patient 14, IMD 16 may deliver defibrillation shocks and other therapies to heart 12 via percutaneous leads that extend through the skin of patient 14 to a variety of positions within or outside of heart 12.

In other examples of therapy systems that provide electrical stimulation therapy to heart 12, a therapy system may include any suitable number of leads coupled to IMD 16, and each of the leads may extend to any location within or proximate to heart 12. For example, other examples of therapy systems may include three leads located as illustrated in FIGS. 1 and 2, and an additional lead located within or proximate to left atrium 33. Other examples of therapy systems may include a single lead that extends from IMD 16 into right atrium 26 or right ventricle 28, or two leads that extend into a respective one of the right atrium 26 and right ventricle 28.

Figure 3:
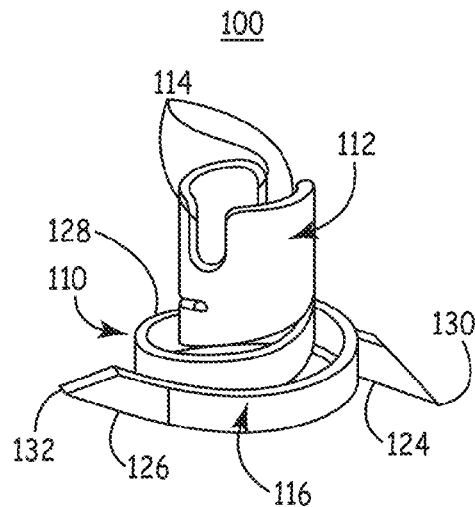
FIG. 3 illustrates an embodiment of a lead anchoring clip in accordance with principles of the present disclosure.

FIG. 3 illustrates one configuration of a lead anchoring clip 100 in accordance with principles of the present disclosure for use in anchoring a lead (not shown) in tissue, such as the atrial septum, for example. The configuration depicted in FIG. 3 shows the clip 100 in a relaxed or pre-deployment state. In use, and as described below, the clip 100 is deflectable or collapsible from the undeflected state of FIG. 3 to a collapsed state, and will self-revert from the collapsed state to or toward the undeflected state. In at least the undeflected state, the clip 100 includes or defines a central hub portion 110 that is coupled to a lead engagement mechanism 112 and an anchoring portion 116. The lead engagement mechanism 112 may further include a torque inducing detent 114 whereas the anchoring portion 116 may include a first leg or prong 124, and a second leg or prong 126. Details on the components are provided below. In general terms, however, the central hub portion 110 has a perimeter 128 defining a circular or circle-like shape. The legs 124, 126 project outwardly relative to the perimeter 128, with the first leg 124 terminating at a tip 130, and the second leg 126 terminating at a tip 132. In this regard, the legs 124, 126 extend in or with an identical wind direction, such that the clip 100 has, in some embodiments, a hurricane-like shape (as best reflected by the top plan view of FIG. 4A).

The wind direction associated with each of the legs 124, 126 is either clockwise or counterclockwise relative to the circle-like shape of the perimeter 128. The perimeter 128 may or may not be continuous, and may or may not reflect a true circle; relative to a two-dimensional top (or bottom) plan view, however, the perimeter 128 of the central hub portion 110 establishes a basis from which clock-type directional attributes (e.g., wind direction) can be identified. For example, the first leg 124 extends from the perimeter 128 at a point of departure 134, terminating at the tip 130. The point of departure 134 can be defined as a point along the leg 124 at which a lateral spacing between the leg 124 and the perimeter 128 begins to increase.

Figure 4A:
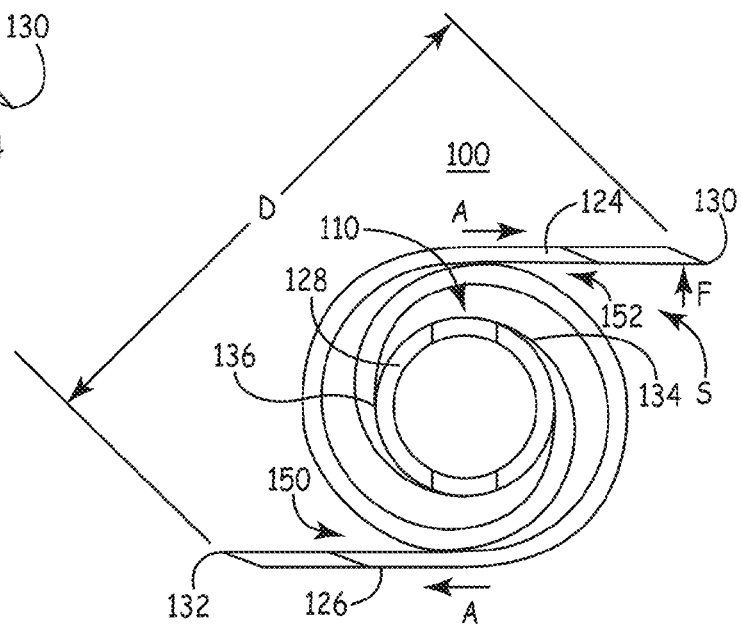
FIGS. 4A-B depict planar views of an embodiment of a lead anchoring clip in accordance with principles of the present disclosure.
Figure 4B:
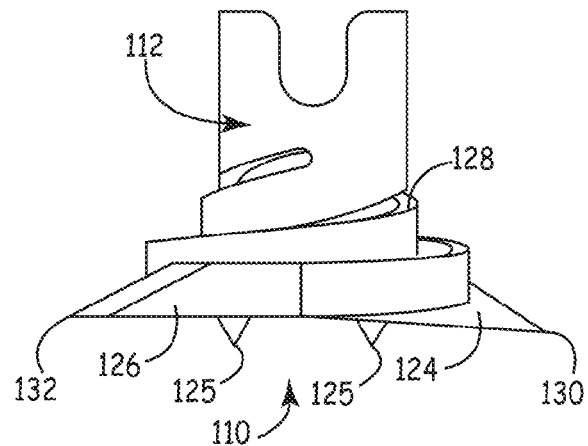

With these conventions in mind, FIGS. 4A-4B illustrate plan views of the clip 100. FIG. 4A depicts the first leg 124 as establishing a wind direction (represented by the arrow "A") that is clockwise. Extension of the second leg 126 relative to the perimeter 128 from a point of departure 136 similarly defines the same clockwise wind direction A. Alternatively, the wind direction established by both of the legs 124, 126 can be counterclockwise.

In some embodiments, the legs 124, 126 can have an identical construction/dimensions. Thus, the legs 124, 126 can define an identical curvature in extension from the perimeter 128. Alternatively, the legs 124, 126 can have differing dimensions and/or curvatures. Similarly, one or both of the legs 124, 126 can have a linear segment or be entirely linear (i.e., extend tangentially from the perimeter 128). Regardless, the wind direction A of the legs 124, 126 are identical.

As best shown in FIG. 4A, the legs 124, 126 are in some embodiments, positioned opposite one another relative to the perimeter 128. Thus, the point of departure 134 of the first leg 124 is opposite the point of departure 136 of the second leg 126. Stated otherwise, relative to an imaginary horizontal axis intersecting the perimeter 128 and a center point of the central hub portion 110, the clip 100 is symmetrical. In other embodiments, however, the legs 124, 126 can be non-uniformly spaced about the perimeter 128 (e.g., relative to the conventions of FIG. 4A, the point of departure 136 of the second leg 126 can be located at a point other than the 6 o'clock position shown). In yet other embodiments, three or more of the legs 124, 126 can be provided that may or may not be equidistantly spaced about the perimeter 128.

In some embodiments, the legs 124, 126 are co-planar with the perimeter of the central hub portion 110 in the undeflected state. As shown in the illustration of FIG. 4B, the legs 124, 126 extend in a plane defined by a face of the central hub portion 110. Alternatively, however, the legs 124, 126 can be constructed to project out of a plane of the central hub portion 110 in the undeflected state. In alternative embodiments, the face of central hub portion 110 may also include one or more barbs 125 for piercing through tissue. During use, the barbs 125 may facilitate anchoring of the clip 100 by preventing unwinding of the clip.

Returning to FIG. 4A, the clip 100 is constructed such that the legs 124, 126 elastically resist movement away from the perimeter 128, both axially and radially relative to the perimeter 128. For example, a radial or lateral spacing S is defined between an inner surface 150 of the first leg 124 and a region 152 of the perimeter 128 closest to the inner surface 150. As a point of reference, relative to any one point along the inner surface 150, a minimum lateral spacing S is established relative to the closest, adjacent point along the perimeter 128, with lateral spacing S increasing from the point of departure 134 to the tip 130. With this in mind, the affinity of the first leg 124 to resist laterally outward movement relative to the perimeter 128 is characterized by the leg resisting a force tending to increase the lateral spacing S. In other words, a force (generically represented by an arrow "F" in FIG. 4A) exerted or experienced along the inner surface 150 tends to cause the first leg 124 to move in a direction opposite the wind direction A. Construction of the clip 100 causes the first leg 124 to resist this unwinding-type force. Instead, the first leg 124 (as well as the second leg 126) slightly deflects in response to the force F, causing material (such as tissue) within the lateral spacing S to gather or pinch between the inner surface 150 and the region 152 of the perimeter 128 as described below.

In the undeflected state, a maximum outer dimension D of the clip 100 is defined as a linear distance between the first and second tips 130, 132. The outer dimension D can vary, and is selected in accordance with the particular procedure(s) for which the clip 100 will be used. For example, for applications in which the clip 100 is anchored in the atrial septum, the tip-to-tip distance D can be on the order of 10-15 mm, thereby ensuring sufficient tissue interface. Alternatively, other maximum outer dimensions D are also acceptable. Regardless, the clip 100 is collapsible from the undeflected state to a collapsed state in which the maximum dimension D is greatly reduced.

Exemplary embodiments of the central hub portion 110 can further be described as including or being formed integrally with a lead engagement mechanism 112. Generally speaking, the lead engagement mechanism 112 can assume a variety of forms, with the predicate being that the structure is configured to engage a portion of a lead (not shown). For example, lead engagement mechanism 112 is a hollow, tubular-like structure that is coupled to, or integrally formed with anchoring portion 116 and central hub portion 110. The lead engagement mechanism 112 may have an internal diameter DI of approximately 3 mm, although the dimension DI is generally dependent on the external diameter of a lead with which the lead engagement mechanism 112 is utilized. In some embodiments, lead engagement mechanism 112 is also configured for interface with a placement device (described below), such as through a torque inducing detent 114, to facilitate transfer of a torque or rotational force applied to the central hub portion 110 and the clip 100 in general.

In the illustrative exemplary configuration, the lead engagement mechanism 112 is centrally positioned within the circle-shape perimeter 128, and bisects an imaginary line connecting the points of departure 134, 136. A torque or rotational moment force applied to the torque inducing detent 114 is relatively uniformly distributed onto the central hub portion 110 and thus onto each of the arms 124, 126. Alternatively, the lead engagement mechanism 112 can be asymmetrically positioned relative to the arms 124, 126 and/or can assume a variety of other configurations.

Stated otherwise, the lead engagement mechanism 112 is a tubular structure having a circumference that is closely aligned with the circumference of the inner most helical section of the anchoring portion 116. That circumference, of the inner most helical section, generally forms the perimeter 128. The first and second legs 124, 126 can be thought of as expanding from a point of departure along the perimeter 128. With reference to FIGS. 3 and 4A, the point of departure is the location along the anchoring portion 116 at which the radius of curvature significantly increases (e.g., greater than 25 percent). Thus the radius of curvature of the anchoring portion 116 is less than the radius of curvature of each of first and second legs 124, 126, with the point of departure being defined as a location along the perimeter where the radius of curvature significantly increases.

The winding of the two segments defining first and second legs 124, 126 is such that the segments partially circumferentially overlap one another in a spiral-like manner. With this construction, as the first leg 124 is forced away from the perimeter 128 (i.e., unwound), a slight circumferential gap will be formed (or an existing gap will be enlarged) between the first leg 124 and the anchoring portion 116. Similarly, a circumferential gap is created and/or expanded between the second leg 126 and the anchoring portion 116 with forced movement of the second leg 126 away from the perimeter 128. As described below, these gaps effectively serve as pathways for forced gathering of tissue within the anchoring portion 116 in connection with anchoring of a lead and sealing of the lead entry point on the septal wall.

The formation of the clip 100 as described in the embodiments above can assume a variety of forms. The distinct constituent segments (e.g., legs, anchoring portion, lead engagement mechanism) can each be formed independently and assembled into a final assembly of clip 100 or the entire clip 100 can be formed from one integral structure. As an example, the exemplary embodiment of clip 100 shown in FIG. 3 can be understood as being constructed from a single tube. In the embodiment, first and second legs 124, 126 segments may be formed from the tube by laser cutting a double helix at a distal portion of the tube. Alternatively, the segments can be made by any suitable process appropriate for a particular material. The two leg segments are then wound, in a variable-pitch, onto themselves in a double-helical configuration to form an expanding diameter helical coil, or anchoring portion 116 as illustrated in FIG. 3. For example, the double helix can be placed in a forming fixture that sets a variable-pitch expanding diameter coil from each of the helical portions with the two coils so formed overlapping. The ends or tips 130, 132 are sharpened for piercing tissue. A proximal portion of the remainder of the tubular structure is formed into the lead engagement mechanism 112 and optionally molded to include torque inducing detent 114.

Figure 5A:
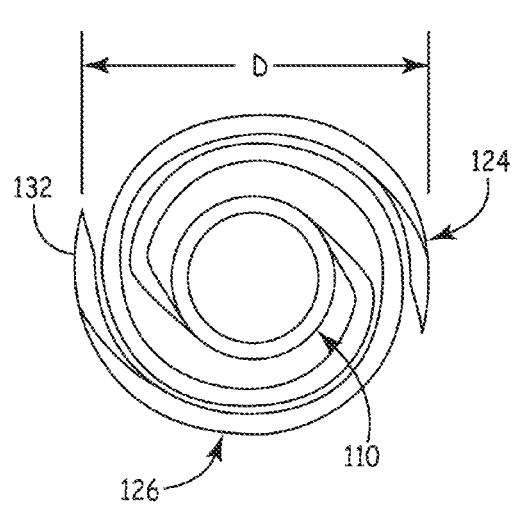
FIG. 5A illustrates an alternative configuration of a lead anchoring clip in accordance with principles of the present disclosure.
Figure 5B:
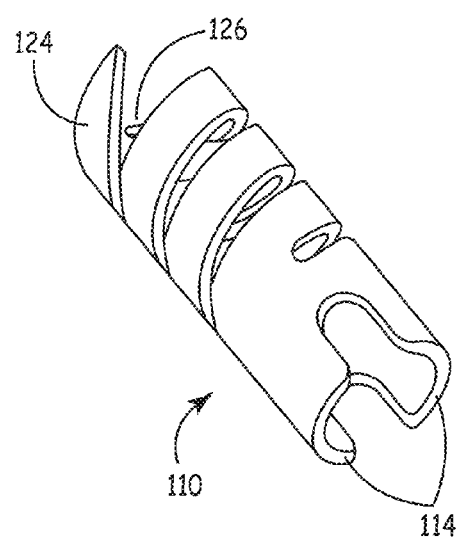
FIG. 5B illustrates another alternative configuration of a lead anchoring clip in accordance with principles of the present disclosure.

FIG. 5A illustrates one collapsed state of the clip 100 in which the legs 124, 126 have been forced to wrap onto the central hub portion 110. Alternatively, FIG. 5B illustrates a differing collapsed state of the clip 100 in which the legs 124, 126 are forced longitudinally away from the central hub portion 110, as well as circumferentially collapsed toward one another. Other collapsed states can also be provided. In any of the collapsed states, the maximum dimension D (referenced in FIG. 5A, for example) of the clip 100 is reduced as compared to the maximum dimension D in the undeflected state, such that the collapsed clip 100 is more readily delivered to a confined surgical site, such as via a catheter or similar body as described below. Further, upon removal of the force(s) otherwise causing the clip 100 to the collapsed state, the clip 100 self-reverts back to the undeflected state.

An ability of the clip 100 to self-revert from a collapsed state to the undeflected state is provided, in some embodiments, by forming the clip 100 from an elastic material, such as stainless steel, and in other embodiments, a super elastic material such as a shape memory alloy. For example, suitable materials for fabrication of the clip 100 include, but are not limited to, nickel titanium alloys (NiTi or NITINOL), cobalt-chromium alloys, stainless steel, ELGILOY, MP35N or other super elastic, and/or shape memory materials that are well known to those skilled in the art of clinical medical devices. Alternatively, the lead anchoring clips could be made from other non-super elastic or non-shape memory materials as desired. Alternatively, other biocompatible elastic or super elastic materials can also be employed. In some embodiments, the clip 100 is formed of a bioresorbable material that will slowly dissolve over time. Alternatively or in addition, the clip 100 can include a biocompatible coating and/or can contain a drug or therapeutic agent that releases over time.

Figure 6A:
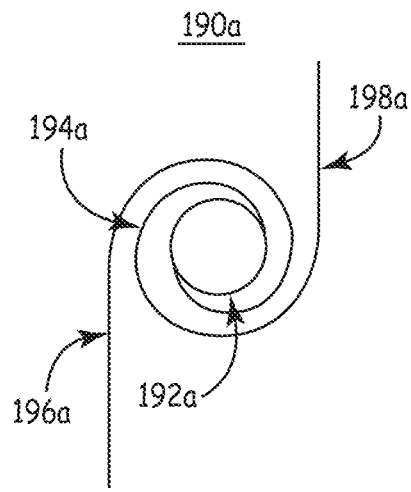
FIG. 6A-6B depict alternative embodiments of lead anchoring clips in accordance with principles of the present disclosure.

An alternative lead anchoring clip 190a in accordance with principles of the present disclosure is shown in FIG. 6A. The clip 190a is akin to the clip 100 (FIG. 3) previously described, and in the undeflected state of FIG. 6A includes a central hub portion 192a having or defining an approximately circular-shaped perimeter 194a from which first and second legs 196a, 198a project. As compared to the clip 100, the legs 196a, 198a extend in a substantially tangential fashion relative to a circumference of the circle-like perimeter 194a, and are relatively linear (relative to a top plan view of FIG. 6A). However, extension of the legs 196a, 198a relative to the perimeter 194a defines a wind direction, with the wind direction for both of the legs 196a, 198a being identical (i.e., counterclockwise relative to the orientation of FIG. 4).

Figure 6B:
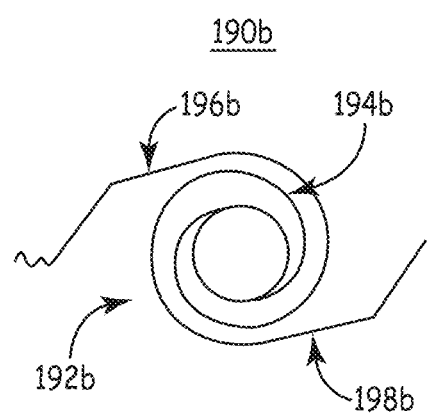

Yet another alternative embodiment of a lead anchoring clip 190b in accordance with principles of the present disclosure is provided in FIG. 6B. As with previous embodiments, the clip 190b includes a central hub portion 192b defining a substantially circle-like perimeter 194b from which a first and a second leg 196b, 198b extend. Extension of each of the legs 196b, 198b establishes a wind direction relative to the circular perimeter 194b, with the wind directions of the legs 196b, 198b being identical (e.g., counterclockwise relative to the orientation of FIG. 6B). In this embodiment, each of the legs 196b, 198b is formed having at least a first bend thereby causing legs 196b, 198b to have at least a first and a second portion oriented in varying directions. The difference of curvature, if any, promotes a more gradual introduction of tissue into the central hub portion 192b as described below.

Regardless of an exact construction of the lead anchoring clip, other aspects of the present disclosure relate to anchoring an implantable medical electrical lead with a clip, while promoting the sealing of an entry point of the lead through tissue in a patient.

FIG. 7 is a plan view of one embodiment of an improved lead. The bipolar lead 200 of this embodiment is stylet-activated, and includes an active fixation mechanism. Lead 200 further includes a flexible, elongate lead body 212 covered by an insulative sleeve, such as polyurethane or silicone rubber. Terminal assembly 214 is provided at the proximal end for coupling lead 200 to an IMD 16 (FIG. 1). Terminal assembly 214 has sealing rings 216 and terminal pin 218, all of a type known in the art. A lead anchoring clip 230 (described above) is provided for coupling lead body 212 to body tissue.

The lead 200 of FIG. 7 is further shown to include a stylet guide 222 and a stylet assembly 224 coupled to terminal pin 218. The stylet assembly 224 imparts stiffness to lead 200 during placement. The stylet further actuates fixation helix 228 in a manner known in the art, one example of which can be found in U.S. Pat. No. 6,909,920, Lokhoff et al., incorporated herein by reference in its entirety. Stylet guide 222 and stylet assembly 224 are typically discarded after use and before connection of terminal pin 218 to IMD 16 (FIG. 1). Other types of stiffening members as known in the art may be used in the alternative for this purpose.

An electrode and fixation assembly designated generally as 226 is disposed at the distal end of lead body 212. In the illustrated embodiment, lead 200 is of the multi-polar, single pass configuration as may be adapted for placement in the coronary sinus or another vessel. The assembly 226 includes a distal helix electrode 228, and a ring electrode 229 positioned proximal to the distal end. As will be appreciated by those of ordinary skill in the art, helix electrode 228 and ring electrode 229 are coupled to separate, insulated lead conductors (not shown in FIG. 7) that extend substantially the length of lead body 212. Lead conductors are preferably configured as concentric multi-filar coils of a platinum-iridium alloy or any other suitable alloy, such as MP35N. This configuration allows for a longitudinal lumen that extends along the length of lead body 212 and that is adapted to receive stylet assembly 224. The lead 200 may include one or more additional electrodes such as described with reference to (FIGS. 1-2).

In the exemplary embodiment, a conventional lead fixation technique is exemplified by the helix 228. The technique involves advancing the helix into the endocardial vessel wall as is known in the art. However, in accordance with the principles discussed in this disclosure, it may be desirable to employ a lead fixation technique at a portion other than the distal end that will also facilitate sealing the vessel wall.

Turning now to FIG. 8, a cutaway side view of the lead anchoring clip and lead assembly of FIG. 7 is illustrated. For ease of illustration and discussion, it should be noted that the various constituent internal components of a medical electrical lead have not been shown. The lead anchoring clip 230 is depicted in a pre-deployment/undeflected state with a first leg 232 and a second leg 234 being relaxed outwardly from the perimeter 236. The lead anchoring clip 230 may be coupled to the lead body 212 through a lead engagement mechanism 238. In an embodiment, indirect coupling between the lead body 212 and the lead engagement mechanism 238 may be achieved through compression of the outer surface of lead body 212 by the inner surface of mechanism 238 when the lead anchoring clip 230 is in use. Alternative embodiments may utilize a direct coupling such as a fixation agent or a snap fit union to create the bond between lead body 212 and mechanism 238 while yet other embodiments may employ sutures to affix mechanism 238 to lead body 212. Regardless of the coupling technique employed, the lead engagement mechanism 238 facilitates a secure union between the clip 230 and the lead body 212 such that fixation of the clip 230 to tissue will result in the anchoring of the lead 200 at the anchoring location.

In alternative embodiments, coupling of the lead 200 to lead anchoring clip 230 may also or additionally be achieved through the central hub portion of the clip upon deployment. As described in more detail below, rotation of the lead anchoring clip causes winding of the spiral portion thereby effectively constricting the central hub portion 110. Thus, the central hub portion 110 may be dimensioned to selectively couple the lead 200 when deployed.

Many of the embodiments of a lead and lead anchoring clip assembly shown and described herein are preferably configured to be deployed via a placement device such as a tubular, flexible placement device (described below in FIGS. 9 and 10) that can be guided either alone or over in conjunction with a guidewire and/or a delivery catheter to a delivery location within a patient. A delivery catheter for use in delivering and deploying such an assembly preferably comprises an internal diameter that is at least as large as the outer diameter of the placement device. One such delivery catheter is described in commonly assigned and co-pending U.S. patent application Ser. No. 12/916,345 corresponding to US Patent publication No.: 2012/0109079, incorporated herein by reference in its entirety. The delivery catheter of U.S. patent application Ser. No. 12/916,345 is a transseptal catheter delivery system that facilitates transvenous delivery of a lead into the left ventricle such as through the atrial septum. Another exemplary delivery catheter that may be employed in conjunction with the placement device of the present disclosure is described in U.S. Pat. No. 7,321,798, incorporated herein by reference in its entirety, which facilitates placement of a lead in the left ventricle with access through ventricular septum. In some embodiments, a delivery catheter can be configured to be sufficiently large in diameter to allow the catheter to be filled with a continuous column of fluid. This advantageously allows for simultaneous monitoring of a fluid pressure at the distal end of the catheter through the continuous fluid column within the catheter. Such an arrangement would also advantageously allow for the injection of a radiographic contrast medium through the delivery catheter in order to determine the precise location of the catheter tip in the cardiovascular system. The skilled artisan will recognize that other embodiments of placement devices can also be used to deliver the improved leads of the present disclosure.

With this in mind, FIGS. 9 and 10 are cross sectional views illustrating but one of an exemplary placement device for the improved lead and lead anchoring clip assemblies described herein. In general terms, placement device 300 is akin to a catheter-type device, and is configured to selectively maintain lead anchoring clip 100 in a collapsed state (it being understood that the clip 100 is shown in the undeflected state in FIG. 10), as well as placement and manipulation of the clip 100 during use.

In some embodiments, the placement device 300 includes a sheath assembly 310 and a handle assembly 316. In general terms, the sheath assembly 310 includes a drive tube 312 sized to slidably receive lead 200 and a sheath cover 314 sized to slidably receive the lead anchoring clip 100. The drive tube 312 is slidably disposed within the sheath cover 314 and is configured to selectively retain the clip 100. The handle assembly 316 facilitates transmission of a user-applied force onto the drive tube 312, and thus onto the clip 100 when the clip 100 is otherwise engaged with the drive tube 312. In general terms, the handle assembly 316 serves as a handle or grip for a user to easily grasp, facilitating user manipulation of the drive tube 312 (e.g., to effectuate rotational, distal or proximal sliding movement of the drive tube 312 relative to the sheath cover 314). Further, the handle assembly 316 allows a user to manipulate the clip 100 in a desired fashion as described below. With this configuration, the sheath cover 314 retains the clip 100 both within and distally in the sheath cover 314.

The handle assembly 316 includes a first handle 325 and a second handle 327. In the exemplary embodiment, the first handle 325 is fixedly mounted to a proximal end of drive tube 312, and provides a grip surface for a user to apply a torque to the drive tube 312. The second handle 327 may also be fixedly coupled to a proximal location of the sheath cover 314, and is independently-movable in relation to the first handle 325. The device 300 is constructed and assembled such that drive tube 312 and the sheath cover 314 can be moved independently in a longitudinal orientation, relative to each other, via operation (e.g., sliding) of the first handle 325 while holding the second handle 327 in a fixed position. Generally, the sheath cover 314 and drive tube 312 are assembled such that the operation of the first handle 325, through rotational movement for example, provides a torque that is translated onto the drive tube 312. However, any other torque-inducing operation that permits manipulation of drive tube 312 within to the sheath cover 316 can be substituted.

The construction of the drive tube 312 and sheath cover 314 can be akin to a catheter, sized for insertion into a blood vessel or other bodily lumen. Alternatively, the sheath cover 314 can have larger dimensions (e.g., akin to a cannula for laparoscopic or other minimally invasive applications). Both the drive tube 312 and sheath cover 314 are thus tubular bodies each defining a lumen, with diameter DL and DD, respectively. Each of the lumens extends from a distal end 320 to a proximal end 322 (referenced generally in FIG. 9).

The lumen of the sheath cover 314 is sized, at the distal section 320, to force and maintain the clip 100 at a desired outer dimension (i.e., collapsed state) appropriate for advancement through the patient's vasculature (or other pathway) as described below. In addition, the distal section 320 of the sheath cover 314 may exhibit sufficient circumferential structural strength or integrity to maintain the clip 100 in the desired collapsed state.

The sheath cover 314 can be formed from a variety of biocompatible materials exhibiting sufficient flexibility for traversing a patient's vasculature in a substantially atraumatic manner. In some embodiments, the distal section 320 can be formed of a more rigid material as compared to a remainder of the sheath cover 314 to better force and maintain the clip 100 in the collapsed state. For example, the distal section 320 can be formed of stainless steel or other metal, whereas a remainder of the sheath cover 316 is formed of a more flexible material, such as nylon, pebax, or a polymeric braided tube. Alternatively, the sheath cover 314 can be a homogenous body.

The diameter DL of the lumen of drive tube 312 at the distal section 320 is sized to slide over the lead 200 while maintaining contact with the lead anchoring clip 100. In the illustrative embodiment, the contact is between the torque inducing detent 114 of the clip 100 and a correspondingly sized notch 324 on the drive tube 312. The material used to construct the drive tube may be similar to that used in the construction of the sheath cover 314.

The drive tube 312 is an elongated body, at least a portion of which is sized to be slidably received within the lumen of the sheath cover 314. It should be understood that the detent 114/notch 324 combination is but one exemplary configuration for providing desired selective connection/torque of the clip 100 by placement device 300. A wide variety of other constructions are also acceptable, so long as a sufficient connection with the clip 100 is achieved for transmitting a torque from the device 300 onto the clip 100.

The handle assembly 316 can be separately formed and subsequently assembled to a remainder of the sheath assembly 310. For example, the handle assembly 316 can be formed with a portion having a rigid material for ease of handling and manipulation during use (e.g., stainless steel, Nitinol, etc.), whereas a remainder of the handle assembly 316 is formed of a material akin to that used to construct the sheath assembly 310. In this exemplary embodiment, the handle assembly 316 is sufficiently compliant and has the structural strength for transmitting an applied torque onto the clip 100. Alternatively, the handle assembly 316 can be formed as an integral, homogenous body so long as a torqueable attribute is provided (e.g., a rotational force applied at a proximal end of the handle assembly 316 is transmitted to the distal end 320).

In alternative embodiments, a locking device (not shown) can be included in the handle assembly 316 to selectively affix the first handle 325 in relation to second handle 327 and prevent movement of the drive tube 312 within the sheath cover 314 during navigation through the vasculature. The locking device would then be selectively released to permit the deployment once the assembly is situated in the desired location. Such a locking device would assume a wide variety of forms appropriate for locking and releasing the first handle 325 and second handle 327.

FIGS. 11-17 are perspective views illustrating an exemplary embodiment of a sequence of steps for deploying and anchoring a lead and anchor assembly at a target tissue site such as an atrial septum. Although the exemplary embodiment illustrates anchoring a lead in a septum wall, it should be noted that the principles apply to any other tissue site.

Figure 12:
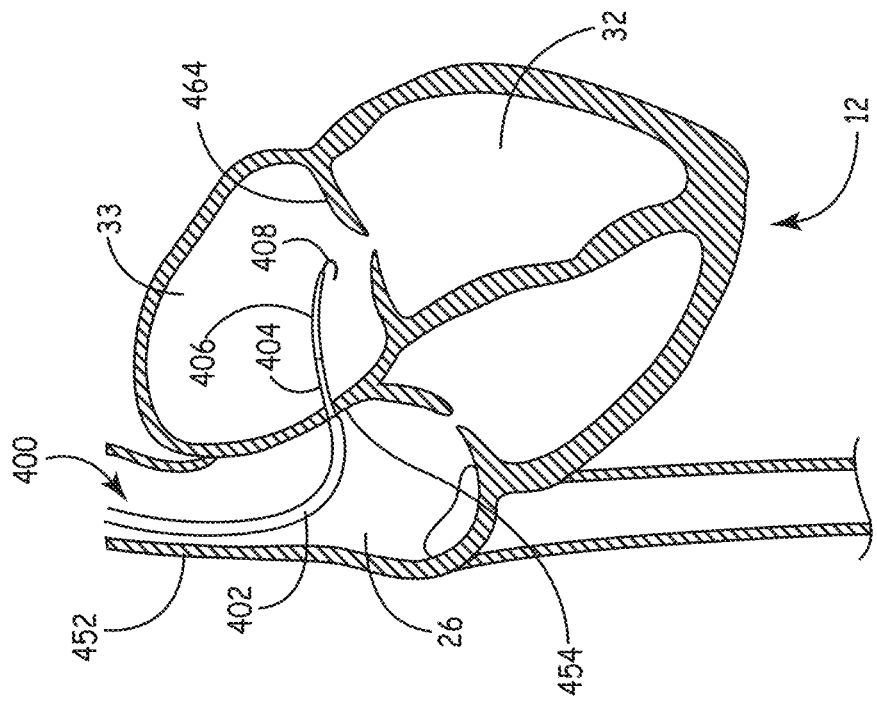
FIGS. 11-17 are perspective views illustrating an exemplary embodiment of a sequence of steps for deploying and anchoring a lead and anchor assembly at a target tissue site.
Figure 11:
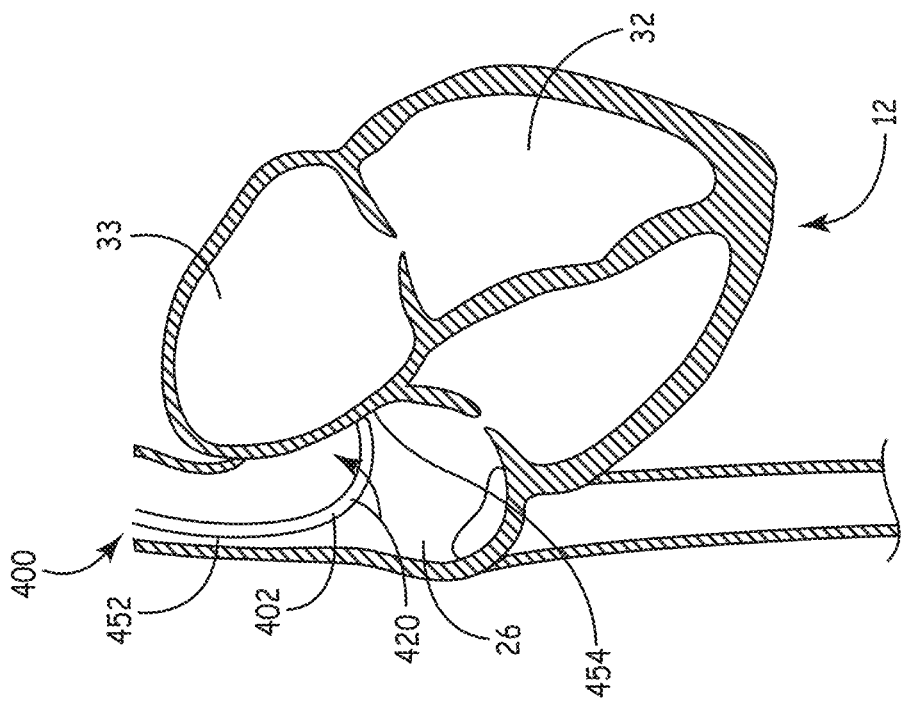
Figure 13:
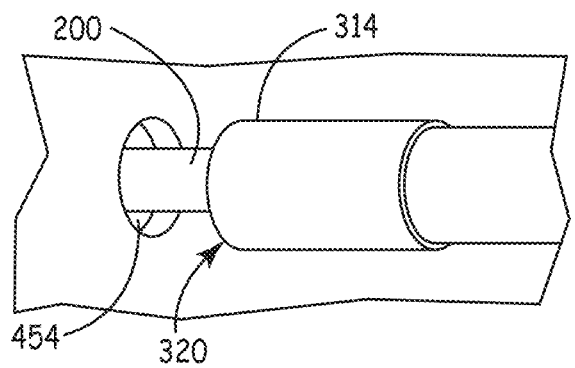

Referring first to the exemplary embodiment of FIGS. 11 and 12, a catheter delivery system 400, an example of which is described in U.S. patent application Ser. No. 12/916,345, is advanced into the right atrium 26 of the heart 12 (FIG. 1) via left subclavian vein (not shown) and the superior vena cava 452. The catheter delivery system 400 includes a lumen (not shown) that carries placement device 300 within which the lead anchoring clip 100 is assembled to a lead 200. The catheter delivery system 400 generally includes an elongate first tubular member 402 including an adjustable portion adjacent its distal end. The system 400 further includes a second tubular member 404 (FIG. 12) that is flexible such that it can selectively bend as desired and straighten when advanced through the first tubular member 402 and over a stiffening member 406 (e.g., a dilator). The system 400 also includes a transseptal puncturing tool 408 (FIG. 12), such as a transseptal RF wire.

The method includes advancing the transseptal puncturing tool 408 (or alternatively a simple guide wire) into the right atrium 26, and then tracking the dilator 406, the second tubular member 404, and the first tubular member 402 over the guide 408 through the superior vena cava 452 into the right atrium 26. The method further includes deflecting an adjustable portion 420 of the first tubular member within the right atrium 26 toward the atrial septum 454 of the heart 12. In some embodiments the method optionally includes tenting the atrial septum 454 at or near the fossa ovalis with the second tubular member 404 and/or the dilator 406, and puncturing the atrial septum 454 with the puncturing tool 408. For example, a transseptal RF wire (e.g., Baylis Medical RF wire) can be energized (e.g., 25 W for 2 seconds) to form a small puncture hole in the septum. In some cases, though, an atrial puncture may already be present (from previous puncture, or naturally) and a separate puncture tool is not necessary.

Turning to FIG. 12, the method includes advancing the guide wire or puncturing tool 408 through the atrial septum 454 into the left atrium 33. The stiffening member or dilator 406 and the second tubular member 404 are then tracked over the guide 408 into the left atrium 33, while maintaining the first tubular member 402 in the right atrium 26. At this point, the method includes withdrawing the stiffening member 406 from at least a portion of the second tubular member 404, thereby allowing a portion of the second tubular member 404 to regain its normally curved shape. Upon regaining its curved shape, the outlet at the distal end of the second tubular member 404 is directed toward the mitral valve 464 and the left ventricle 32 of the heart 12.

No matter the final destination or delivery method, one of skill in the art can now appreciate that the a portion of the lead 200 coupled to the lead anchoring clip 100 assembly will be located adjacent or within the atrial septum 454 at some point during the delivery process.

Accordingly, the deployment of the lead anchoring clip 100 coupled to lead 200 is next illustrated in FIGS. 13-17. It may be helpful for the reader to review these illustrations in conjunction with FIG. 9. In the illustration of FIG. 13, a portion of lead 200 has been advanced through the atrial septum 454 (for example as described above) and in the depiction of FIG. 13, the catheter delivery system 400 has been withdrawn from the right atrium. However, as previously explained, a catheter delivery system is only one exemplary implementation of delivering the lead/lead anchoring clip assembly into the heart and it is contemplated that a placement device may be used alone or in conjunction with any other method for delivery. Turning then to the illustration of FIG. 13, the lead anchoring clip 100 (not shown) is encased within the sheath cover 314 of placement device 300 such that the clip 100 is maintained in a wound/collapsed state. In the collapsed state, an effective maximum outer dimension of the clip 100 is reduced to a distance or dimension defined by the diameter DL at the distal end 320.

Figure 14:
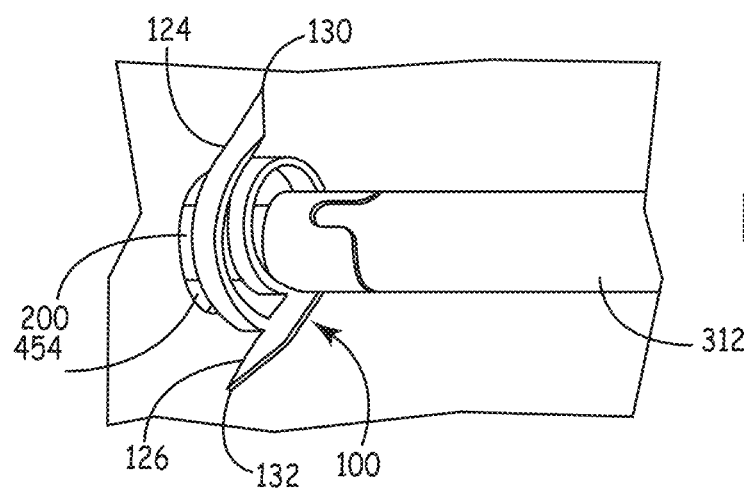

Turning to FIG. 14, once the lead anchoring clip 100 is positioned at the desired tissue location, the sheath cover 314 is retracted to expose/release the clip 100. In other words, sheath cover 314 is moved proximally toward the handle 325, such that the clip 100 is distally beyond or outside of the sheath cover 314. Retraction of the sheath cover 314 also permits the clip 100 to assume its pre-deployment state. To assist in deploying the clip 100 from the sheath cover 314, the locking device 327 can be actuated to cause it to grip drive tube 312, and thus the clip 100, can be rotated (e.g., at approximately 180 degree) through rotation of the handle 325. Once free of the confines of the sheath cover 314, the clip 100 will self-revert to the undeflected state.

Figure 15:
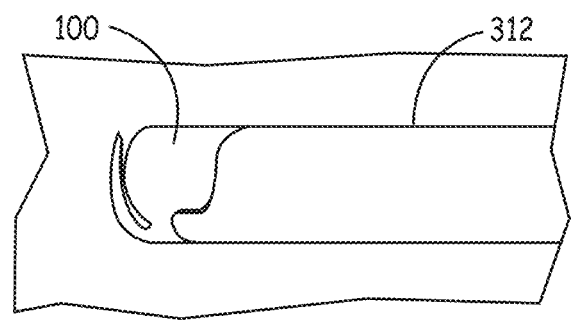

Next, in FIG. 15, once deployed from the sheath cover 314, the clip 100 is rotated via rotation of the handle 325 to engage desired tissue segment(s). In particular, a user-applied torque at the handle 325 is transmitted to the clip 100. Rotation of the clip 100 in the wind direction of the legs 124, 126 causes the tips 130, 132 to engage or pierce into tissue otherwise in contact with the tips 130, 132.

Figure 16B:
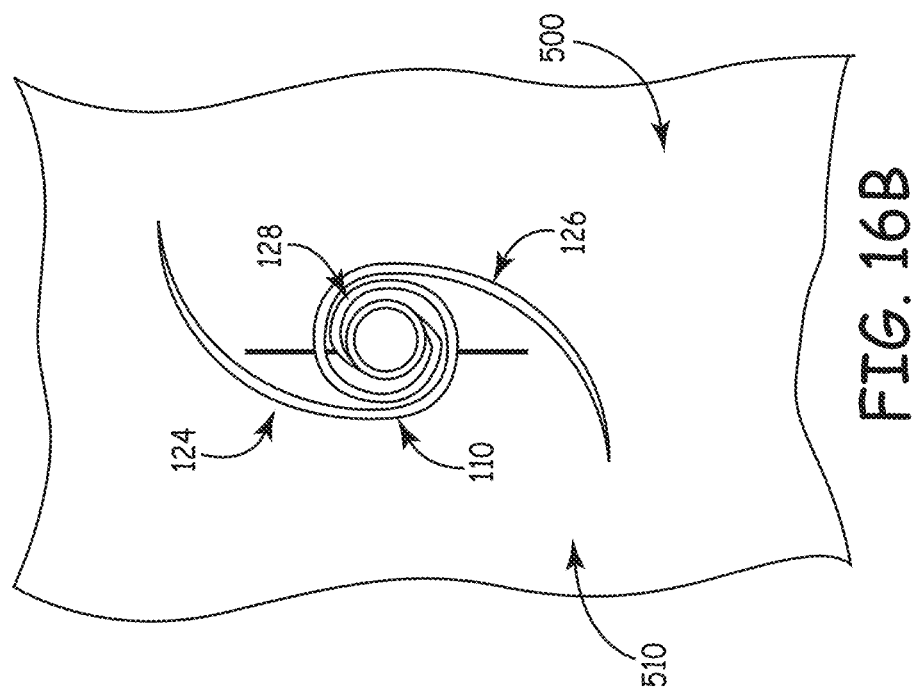
Figure 16A:
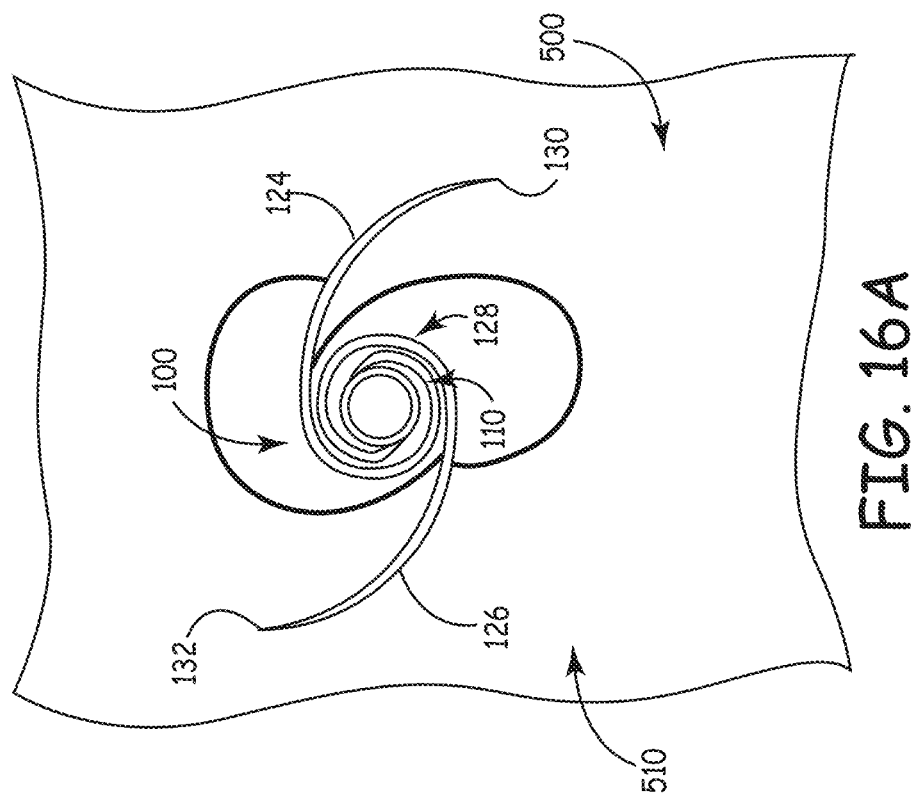

For example, FIG. 16A schematically illustrates opposing tissue segments 500, 510 of atrial septum AS within which the clip 100 is initially deployed. With initial rotation of the clip 100 (in the wind direction of the legs 124, 126, for example clockwise relative to the orientation of FIG. 16), the tips 130, 132 pierce into respective ones of the tissue segments 500, 510 as shown in FIG. 16B. With further rotation of the clip 100, the legs 124, 126 continually pass through an increasing volume of the tissue segments 500, 510, gathering or pinching portions of the tissue segments 500, 510 between the legs 124, 126 and the central hub portion 110, including the perimeter 128, as shown in FIG. 16B. Gaps between the legs 124, 126 and the perimeter 128 effectively serve as pathways, guiding or drawing tissue toward the central hub portion 110. Thus, following rotation of the clip 100 to a desired extent, the tissue segments 500, 510 are drawn together to anchor the clip 100 and thus the lead 200, and in some embodiments seal the lead entry point through the septal wall into the left atrium as shown in FIG. 16B.

Figure 17:
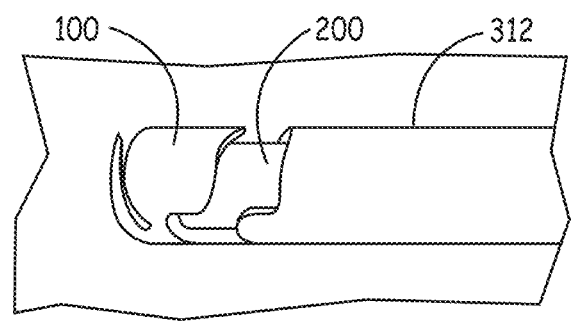

Turning to FIG. 17, once desired rotation of the clip 100 is complete, the clip 100 is released from the drive tube 312. For example, the drive tube 312 can be retracted away from the clip 100. If necessary, the sheath cover 314 can be distally advanced to push against the clip 100 to assist in disengaging the drive tube 312 from the clip 100.

As one skilled in the art can appreciate from the general exemplary principles discussed above, that the clip 100 and related delivery devices and systems can be used in a plethora of implementations to anchor various devices and cause sealing of holes in tissue from defects and as a result of various procedures. In some aspects of the present disclosure, the anchoring clips may even be formed of bioresorbable materials such that the clips will dissolve after passage of time when it is anticipated that the tissue has healed. In other embodiments, it may be desirable to extract the clip after a period of time. Such extractable clips can therefore be envisioned as including an attachment or hole on lead engagement mechanism 112, for example, that could be coupled to a tether to facilitate the extraction process.

Although the present disclosure has been described with reference to preferred embodiments, workers skilled in the art will recognize that changes can be made in form and detail without departing from the spirit and scope of the present disclosure.

What is claimed is:

1. A lead anchoring clip, comprising:
a central hub portion having a circular shaped perimeter defined around a central axis;
a hollow tubular-like structure centrally positioned within the circular shaped perimeter and having an internal diameter sized to engage around an external diameter of a medical electrical lead; and
an anchoring portion including a first leg member extending around the central axis and outwardly from a first point of departure at the perimeter of the hub portion to a terminal tip thereof, and a second leg member extending around the central axis and outwardly from a second point of departure at the perimeter of the hub portion to a terminal tip thereof, the first and second leg members extending in the same direction, either clockwise or counterclockwise, partially circumferentially overlapping one another, and each of the first and second leg members forming an expanding diameter helical coil;
wherein the tips of the first and second leg members are coplanar with one another, and each of the first and second leg members having a tapered distal end; and
the first and second points of departure, from which the first and second leg members extend, respectively, are located opposite one another and offset along the central axis from the coplanar tips of the first and second leg members.

2. The lead anchoring clip of claim 1, wherein the central hub portion is formed integrally with the anchoring portion.

3. The lead anchoring clip of claim 1, wherein the hollow tubular-like structure includes a detent configured to interface with a drive tube of a placement device, the drive tube having a lumen diameter sized to slide over the lead, and the interface between the drive tube and the detent being a torque-transmitting contact for inducing rotation of the clip.

4. The lead anchoring clip of claim 2, wherein the hollow tubular-like structure is formed integrally with the central hub portion and the anchoring portion.

5. The lead anchoring clip of claim 1, wherein:
when the clip is in an undeflected state, a maximum outer dimension of the clip is defined by a linear distance between the tips of the first and second leg members of the anchoring portion, the linear distance being orthogonal to the central axis; and
the clip is collapsible from the undeflected state such that the maximum outer dimension is reduced.

* * * * *